US010499999B2

(12) United States Patent
Yu

(10) Patent No.: US 10,499,999 B2
(45) Date of Patent: Dec. 10, 2019

(54) SYSTEMS AND METHODS FOR ALIGNING AN ELONGATE MEMBER WITH AN ACCESS SITE

(71) Applicant: Auris Health, Inc., Redwood City, CA (US)

(72) Inventor: Alan Lau Yu, Union City, CA (US)

(73) Assignee: Auris Health, Inc., Redwood City, CA (US)

( * ) Notice: Subject to any disclaimer, the term of this patent is extended or adjusted under 35 U.S.C. 154(b) by 303 days.

(21) Appl. No.: 14/880,024

(22) Filed: Oct. 9, 2015

(65) Prior Publication Data

US 2016/0100896 A1 Apr. 14, 2016

Related U.S. Application Data

(60) Provisional application No. 62/061,820, filed on Oct. 9, 2014.

(51) Int. Cl.
*A61B 34/30* (2016.01)
*A61B 90/57* (2016.01)

(52) U.S. Cl.
CPC ........ *A61B 34/30* (2016.02); *A61B 2034/301* (2016.02); *A61B 2090/571* (2016.02)

(58) Field of Classification Search
CPC ............. A61B 34/30; A61B 2090/571; A61B 2034/301
USPC ........................................................ 606/174
See application file for complete search history.

(56) References Cited

U.S. PATENT DOCUMENTS

| 4,921,393 | A | * | 5/1990 | Andeen | B23Q 11/0014 414/729 |
| 5,375,588 | A | * | 12/1994 | Yoon | A61B 17/3403 600/114 |
| 5,402,801 | A | * | 4/1995 | Taylor | B25J 9/04 128/898 |

(Continued)

FOREIGN PATENT DOCUMENTS

EP 0 830 562 7/2009

OTHER PUBLICATIONS

Verdaasdonk et al., Jan. 23, 2013, Effect of microsecond pulse length and tip shape on explosive bubble formation of 2.78 μm Er,Cr;YSGG and 2.94 μm Er:YAG laser, Proceedings of SPIE, vol. 8221, 12.

(Continued)

*Primary Examiner* — Julian W Woo
(74) *Attorney, Agent, or Firm* — Knobbe, Martens, Olson & Bear, LLP

(57) ABSTRACT

An alignment system for controlling an alignment of a robotically controlled elongate member at an access site on a patient may include a longitudinal support rail and support arms coupled with and extending from the longitudinal support rail to form an alignment joint. One or more of the support arms may be configured to maintain the alignment of the elongate member with the access site during a surgical procedure. A method of aligning an elongate member with an access site may include determining a position of a stabilizer of an alignment joint and the access site on a patient, coupling the stabilizer to the access site on the patient, and automatically aligning the instrument driver with the stabilizer on the patient.

20 Claims, 10 Drawing Sheets

(56) References Cited

U.S. PATENT DOCUMENTS

| | | | |
|---|---|---|---|
| 5,540,648 A * | 7/1996 | Yoon | A61B 17/3403 600/102 |
| 5,746,720 A * | 5/1998 | Stouder, Jr. | A61B 17/3417 604/117 |
| 5,865,809 A * | 2/1999 | Moenning | A61B 17/3403 128/DIG. 26 |
| 6,279,579 B1 | 8/2001 | Riaziat | |
| 6,522,906 B1 | 2/2003 | Salisbury et al. | |
| 6,850,817 B1 * | 2/2005 | Green | A61B 1/00193 348/E13.014 |
| 7,699,855 B2 * | 4/2010 | Anderson | A61B 34/71 606/1 |
| 7,789,874 B2 | 9/2010 | Yu et al. | |
| 8,146,874 B2 | 4/2012 | Yu | |
| 8,469,947 B2 * | 6/2013 | Devengenzo | A61B 1/00149 606/1 |
| 8,491,597 B2 * | 7/2013 | Russell | A61B 34/20 606/130 |
| 8,506,555 B2 * | 8/2013 | Ruiz Morales | B25J 9/041 606/1 |
| 8,968,333 B2 | 3/2015 | Yu et al. | |
| 9,226,796 B2 | 1/2016 | Bowling | |
| 9,314,306 B2 | 4/2016 | Yu | |
| 9,326,822 B2 | 5/2016 | Lewis et al. | |
| 9,408,669 B2 | 8/2016 | Kokish et al. | |
| 9,452,018 B2 | 9/2016 | Yu | |
| 9,480,534 B2 | 11/2016 | Bowling | |
| 9,504,604 B2 | 11/2016 | Alvarez | |
| 9,561,083 B2 | 2/2017 | Yu et al. | |
| 9,566,201 B2 | 2/2017 | Yu | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,795,445 B2 | 10/2017 | Bowling | |
| 9,818,681 B2 | 11/2017 | Machida | |
| 9,820,818 B2 | 11/2017 | Malackowski | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,004,562 B2 * | 6/2018 | Kostrzewski | A61B 34/70 |
| 10,004,569 B2 * | 6/2018 | Singh | A61B 90/10 |
| 10,016,900 B1 | 7/2018 | Meyer et al. | |
| 10,022,192 B1 | 7/2018 | Ummalaneni | |
| 10,145,747 B1 | 12/2018 | Lin et al. | |
| 10,154,829 B2 | 12/2018 | Henderson et al. | |
| 10,159,532 B1 | 12/2018 | Ummalaneni et al. | |
| 2002/0193685 A1 | 12/2002 | Mate | |
| 2003/0050558 A1 | 3/2003 | Bencini | |
| 2005/0182295 A1 | 8/2005 | Soper et al. | |
| 2006/0079756 A1 | 4/2006 | Lloyd et al. | |
| 2006/0270909 A1 * | 11/2006 | Davis | A61B 17/0218 600/210 |
| 2007/0021738 A1 | 1/2007 | Hasser et al. | |
| 2007/0144298 A1 | 6/2007 | Miller | |
| 2007/0244599 A1 | 10/2007 | Tsai | |
| 2008/0077158 A1 | 3/2008 | Haider et al. | |
| 2008/0245946 A1 | 10/2008 | Yu | |
| 2009/0099445 A1 | 4/2009 | Burger | |
| 2009/0088634 A1 | 5/2009 | Zhao | |
| 2009/0248037 A1 | 10/2009 | Prisco | |
| 2009/0259412 A1 | 10/2009 | Brogardh | |
| 2010/0234999 A1 | 9/2010 | Nakajima | |
| 2011/0040411 A1 | 2/2011 | Murayama et al. | |
| 2011/0060215 A1 | 3/2011 | Tupin | |
| 2011/0144479 A1 | 6/2011 | Hastings et al. | |
| 2011/0208355 A1 | 8/2011 | Tsusaka | |
| 2012/0046542 A1 | 2/2012 | Csavoy et al. | |
| 2012/0071895 A1 | 3/2012 | Stahler et al. | |
| 2012/0191107 A1 * | 7/2012 | Tanner | A61B 6/12 606/130 |
| 2012/0241576 A1 | 9/2012 | Yu | |
| 2013/0041509 A1 | 2/2013 | Saito | |
| 2013/0169423 A1 | 7/2013 | Iorgulescu et al. | |
| 2013/0173058 A1 | 7/2013 | Seo et al. | |
| 2013/0269109 A1 | 10/2013 | Yu | |
| 2014/0039517 A1 | 2/2014 | Bowling | |
| 2014/0052154 A1 | 2/2014 | Griffiths | |
| 2014/0088763 A1 | 3/2014 | Hazan | |
| 2014/0142591 A1 | 5/2014 | Alvarez et al. | |
| 2014/0276389 A1 | 9/2014 | Walker | |
| 2014/0276391 A1 | 9/2014 | Yu | |
| 2014/0276647 A1 | 9/2014 | Yu | |
| 2014/0276935 A1 | 9/2014 | Yu | |
| 2014/0276936 A1 | 9/2014 | Kokish et al. | |
| 2014/0276939 A1 | 9/2014 | Kokish et al. | |
| 2014/0277333 A1 | 9/2014 | Lewis et al. | |
| 2014/0277334 A1 | 9/2014 | Yu et al. | |
| 2014/0309649 A1 | 10/2014 | Alvarez et al. | |
| 2014/0350387 A1 | 11/2014 | Siewerdsen et al. | |
| 2014/0357984 A1 | 12/2014 | Wallace et al. | |
| 2014/0364870 A1 | 12/2014 | Alvarez et al. | |
| 2014/0379000 A1 | 12/2014 | Romo et al. | |
| 2015/0051592 A1 | 2/2015 | Kintz | |
| 2015/0051732 A1 | 2/2015 | Grygorowicz et al. | |
| 2015/0066051 A1 | 3/2015 | Kwon | |
| 2015/0101442 A1 | 4/2015 | Romo | |
| 2015/0119638 A1 | 4/2015 | Yu et al. | |
| 2015/0164594 A1 | 6/2015 | Romo et al. | |
| 2015/0164596 A1 | 6/2015 | Romo | |
| 2015/0239121 A1 | 8/2015 | Takeda | |
| 2015/0248121 A1 | 9/2015 | Nilsson | |
| 2015/0289941 A1 | 10/2015 | Bowling | |
| 2015/0323398 A1 | 11/2015 | Lauzier et al. | |
| 2015/0328771 A1 | 11/2015 | Yuelai et al. | |
| 2015/0335480 A1 | 11/2015 | Alvarez et al. | |
| 2015/0374446 A1 | 12/2015 | Malackowski | |
| 2016/0001038 A1 | 1/2016 | Romo et al. | |
| 2016/0022189 A1 | 1/2016 | Pouteau et al. | |
| 2016/0031083 A1 | 2/2016 | Embon | |
| 2016/0074117 A1 | 3/2016 | Mohr | |
| 2016/0144509 A1 | 5/2016 | Gulhar | |
| 2016/0158601 A1 | 6/2016 | Lee et al. | |
| 2016/0221189 A1 | 8/2016 | Nilsson | |
| 2016/0235946 A1 | 8/2016 | Lewis et al. | |
| 2016/0270865 A1 | 9/2016 | Landey et al. | |
| 2016/0279405 A1 | 9/2016 | Riley | |
| 2016/0287279 A1 | 10/2016 | Bovay et al. | |
| 2016/0296294 A1 | 10/2016 | Moll et al. | |
| 2016/0338785 A1 | 11/2016 | Kokish et al. | |
| 2016/0354582 A1 | 12/2016 | Yu et al. | |
| 2016/0354925 A1 | 12/2016 | Shimodaira | |
| 2016/0374541 A1 | 12/2016 | Agrawal et al. | |
| 2017/0007336 A1 | 1/2017 | Tsuboi | |
| 2017/0007337 A1 | 1/2017 | Dan | |
| 2017/0007342 A1 | 1/2017 | Kasai | |
| 2017/0007343 A1 | 1/2017 | Yu | |
| 2017/0100199 A1 | 4/2017 | Yu et al. | |
| 2017/0105804 A1 | 4/2017 | Yu | |
| 2017/0119413 A1 | 5/2017 | Romo | |
| 2017/0119481 A1 | 5/2017 | Romo et al. | |
| 2017/0165011 A1 | 6/2017 | Bovay et al. | |
| 2017/0165834 A1 | 6/2017 | Hares | |
| 2017/0172673 A1 | 6/2017 | Yu et al. | |
| 2017/0172680 A1 | 6/2017 | Bowling | |
| 2017/0202627 A1 | 7/2017 | Sramek et al. | |
| 2017/0209073 A1 | 7/2017 | Sramek et al. | |
| 2017/0245955 A1 | 8/2017 | Bowling | |
| 2017/0274530 A1 | 9/2017 | Mottram | |
| 2017/0290631 A1 | 10/2017 | Lee et al. | |
| 2017/0333679 A1 | 11/2017 | Jiang | |
| 2017/0340396 A1 | 11/2017 | Romo et al. | |

(56) References Cited

U.S. PATENT DOCUMENTS

| | | |
|---|---|---|
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0228528 A1 | 4/2019 | Mintz et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |

OTHER PUBLICATIONS

Skarecky et al., 2008, Zero positive surgical margins after radical prostatectomy: is the end in sight?, Expert Review of Medical Devices, 5(6):709-717.

\* cited by examiner

SYSTEMS AND METHODS FOR ALIGNING AN ELONGATE MEMBER WITH AN ACCESS SITE

CROSS-REFERENCE TO RELATED APPLICATIONS

This application claims priority to U.S. Provisional Application Ser. No. 62/061,820, titled "Systems and Methods for Aligning an Elongate Member with an Access Site," filed on Oct. 9, 2014. The disclosure of the above-referenced patent application is hereby incorporated by reference in its entirety herein.

This application is related to U.S. patent application Ser. No. 13/174,563, titled "Anti-Buckling Mechanisms and Methods," filed on Jun. 30, 2011; Ser. No. 13/803,535, titled "Active Drives for Robotic Catheter Manipulators," filed on Mar. 14, 2013; Ser. No. 13/803,627, titled "Active Drives for Robotic Catheter Manipulators," filed on Mar. 14, 2013; Ser. No. 13/801,957, titled "Selective Grip Device for Drive Mechanism," filed on Mar. 13, 2013; Ser. No. 13/832,352, titled "Catheter Insertion System and Method of Fabrication," filed on Mar. 15, 2013; Ser. No. 13/833,531, titled "Rotational Support for an Elongate Member," filed on Mar. 15, 2013; Ser. No. 13/835,136, titled "Active Drive Mechanism for Simultaneous Rotation and Translation," filed on Mar. 15, 2013; Ser. No. 13/839,967, titled "Vascular Remote Catheter Manipulator," filed on Mar. 15, 2013; and Ser. No. 13/838,777, titled "Active Drive Mechanism with Finite Range of Motion," filed on Mar. 15, 2013. This application is also related to U.S. Pat. No. 8,602,031, titled "Modular Interfaces and Drive Actuation Through Barrier," filed on Jan. 12, 2009; and U.S. Pat. No. 7,789,874, titled "Support Assembly for Robotic Catheter System," filed on Jul. 1, 2005. All of the above-referenced patents and patent applications are hereby incorporated herein by reference in their entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This invention relates generally to the surgical robotics field, and more specifically to a new and useful system and method for using an alignment joint.

BACKGROUND

Robotic surgical systems and devices are well suited for use in performing minimally invasive medical procedures, as opposed to conventional techniques that may require large incisions to open the patient's body cavity to provide the surgeon with access to internal organs. For example, a robotic surgical system may be used to facilitate imaging, diagnosis, and treatment of tissues that may lie deep within a patient or that may be preferably accessed only via naturally occurring pathways such as blood vessels or the gastrointestinal tract. One such robotic surgical system that may be used in such a minimally invasive procedure is a robotic catheter system. A robotic catheter system uses a robot, external to the patient's body cavity, to insert a catheter through a small incision in a patient's body cavity and guide the catheter to a location of interest.

Typically, elongate members, for example catheters, are inserted into a body of a patient through a small incision or access site. The instrument driver driving the elongate member is aligned with the access site using a device, such as a stabilizer, as described in pending U.S. patent application Ser. No. 13/174,563 (publication number US2012/0071895), which is herein incorporated by reference. However, significant time is spent aligning the instrument driver with the insertion site using the stabilizer. The typical process requires the user to "train" the instrument driver with the location of the access site prior to loading the elongate member at the start of a procedure. This training process involves advancing the instrument driver forward to mark an access site position. Once the instrument driver has been trained, it must then be retracted to a starting position to load on the elongate member. The purpose of this training process is to notify the instrument driver of the location of the access site, such that when it is advancing later with the elongate member attached, it has a known target location. This training process is not a preferred process, because it is time consuming prior to each robotic procedure. It is akin to doing a trial run of each robotic procedure before the start of the procedure. In addition, once the instrument driver has been trained with the access site location, and once the stabilizer is adhered to the insertion site of the patient, the stabilizer cannot be repositioned, even if the patient moves and the instrument driver needs to be repositioned. Further, it is difficult to adhere the stabilizer to skin that is damp, moist or flaccid, for example due to age or weight of the patient.

Thus, there is a need for a new and useful system and method for aligning an elongate member with an access site. This invention provides such a new and useful system and method.

DETAILED DESCRIPTION

The following description of various embodiments of the invention is not intended to limit the invention to these embodiments, but rather to enable any person skilled in the art to make and use this invention.

Described herein are systems and methods for aligning an elongate member with an access site. An elongate member may include a guidewire, sheath, leader, catheter, probe, needle, or any other type of device. As described herein, an elongate member may be aligned with an access site of a patient. An access site may include a port in an artery or vein or a natural orifice, such as the gastrointestinal tract, esophagus, trachea, or any other type of site. In some embodiments, an elongate member may be aligned with an access site using a stabilizer. The stabilizer may be attached, coupled, adhered, or otherwise anchored to the skin of a patient around or near an access site. The stabilizer may include a slot, hole, eyelet, or other opening for receiving the distal end of the elongate member. A distal end of the elongate member may be inserted into the access site of the patient through the stabilizer.

In some embodiments, the stabilizer may be coupled to an alignment joint. The alignment joint supporting the stabilizer may be encoded or include one or more position sensors, such that a position of the access site marked by the stabilizer may be communicated to an instrument driver, active drive device, or anti-buckling device. In some embodiments, a position may be communicated through Wi-Fi, Bluetooth, a hardwired connection, and/or any other communication protocol known to one skilled in the art.

In some embodiments, an elongate member may be driven into the access site of the patient by an instrument driver or active drive device. The instrument driver or active drive device may be attached, coupled, or otherwise fastened to the stabilizer at the access site of the patient. Alternatively, an anti-buckling device for supporting the elongate member may be attached, coupled, or otherwise fastened to the stabilizer at the access site of the patient.

Figure 1:
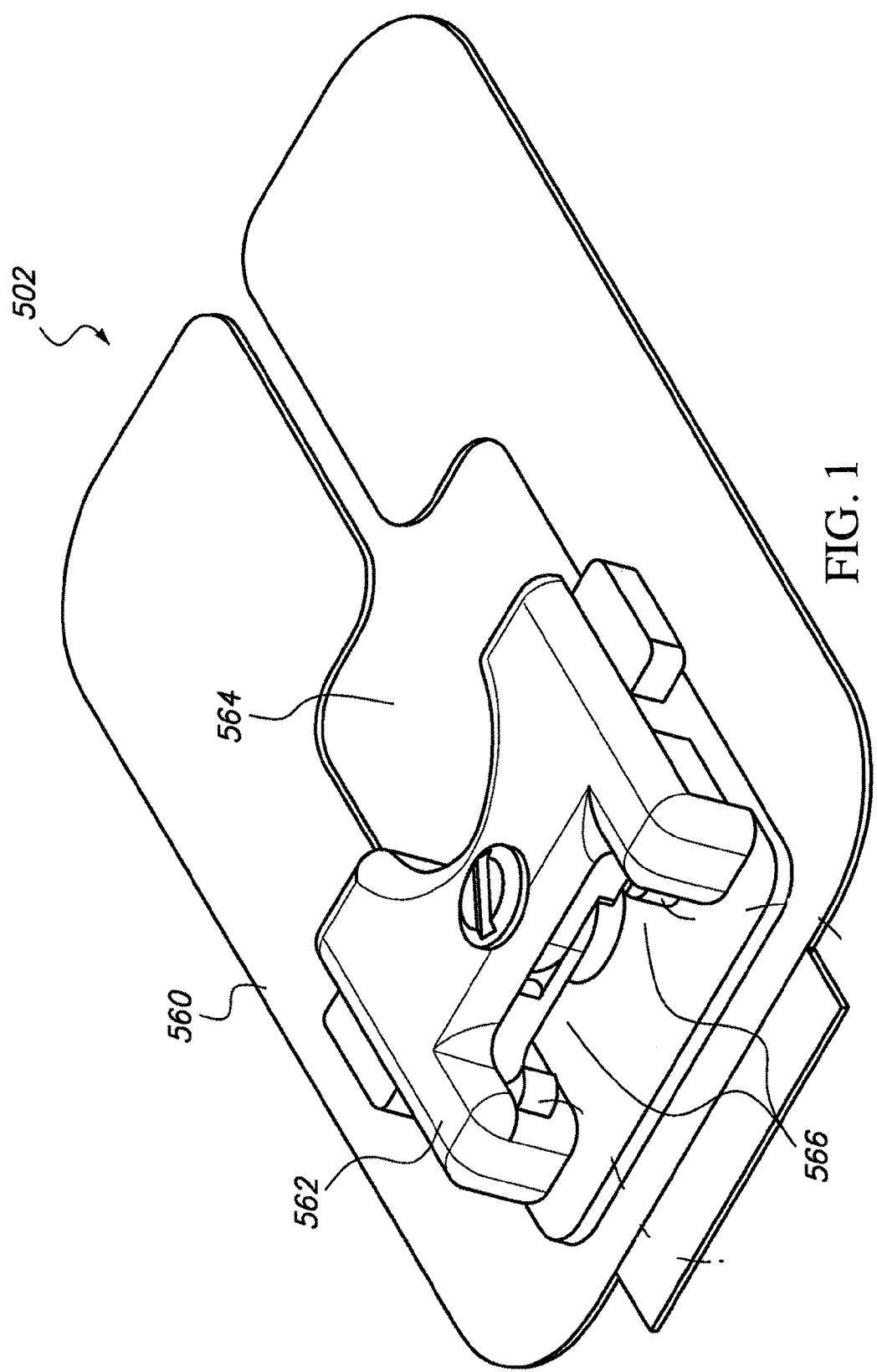
FIG. 1 illustrates a stabilizer, in accordance with one embodiment.

FIG. 1 illustrates a stabilizer 502, in accordance with one embodiment. The stabilizer 502 preferably functions to couple to an alignment joint and to align an elongate member with an access site of the patient. As shown in FIG. 1, the stabilizer 502 may include a base 560 for coupling with the alignment joint. Further, the base 560 may include adhesive at its bottom side for attachment to a patient's skin. In some embodiments, the stabilizer 502 further includes a connector 562 for coupling with an instrument driver, active drive device, or anti-buckling mechanism. In some embodiments, the base 560 may be a high-density polyethylene (HDPE) platform that includes a strain relief material underneath for providing transition from the rigid HDPE material to the patient skin. In some embodiments, the base 560 may also include a butterfly peel-away liner (e.g., tear-resistant HDPE liner) that covers the adhesive material at the bottom side of the platform. During use, the liner may be peeled away to expose the adhesive at the bottom side of the base 560. The stabilizer 502 may also include an opening 564 formed at the base 560 for allowing the elongate member to reach the patient's skin. The opening 564 may include a pair of slots 566 for receiving one or more protrusions from an instrument drive, active drive device, or anti-buckling device.

Figure 2A:
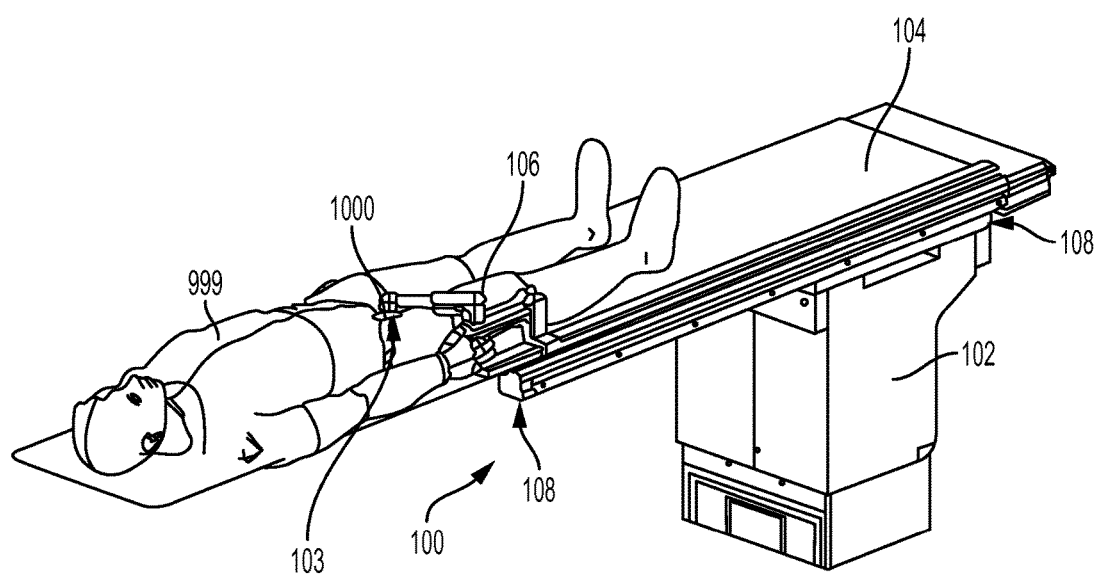
FIGS. 2A-D illustrate perspective views of a surgical system having an alignment joint, in accordance with one embodiment.
Figure 2B:
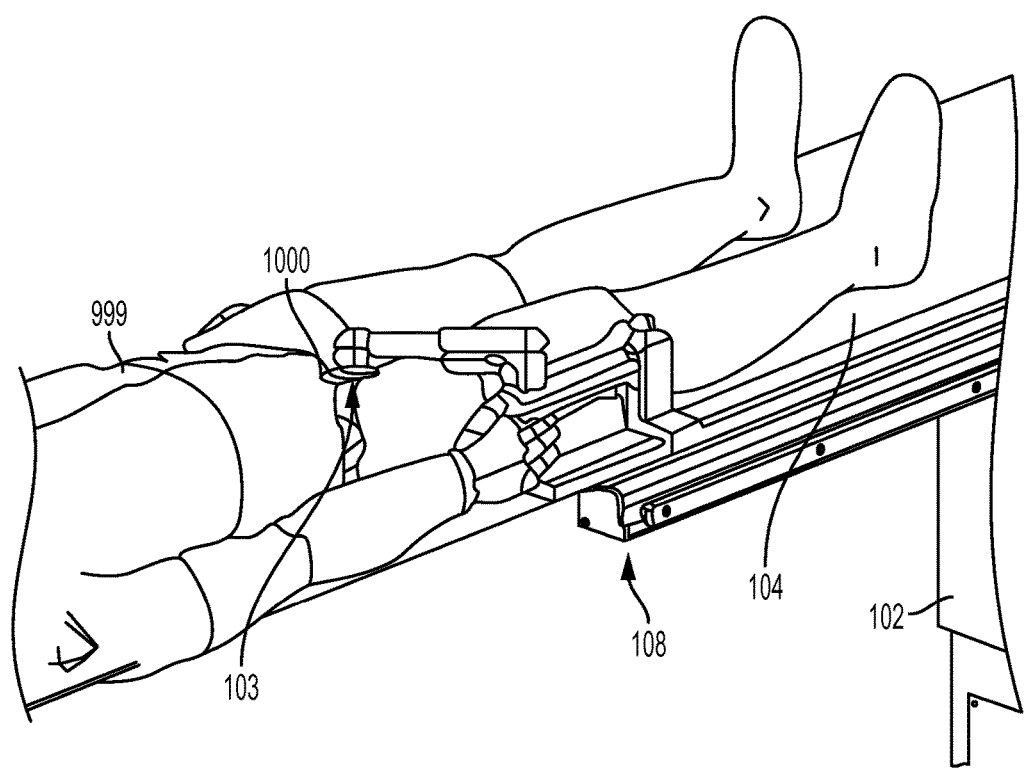

Turning now to FIGS. 2A-2D, an exemplary alignment system 100 is illustrated. As shown in FIG. 2A, an alignment system 100 for controlling an alignment of a robotically controlled elongate member at an access site 1000 of a patient 999 may include a longitudinal support rail 108 and one or more support arms coupled together to form an alignment joint 106, which is coupled to and extends from the longitudinal support rail 108. The alignment joint 106 may be configured to reach the access site 1000 on the patient and to maintain the alignment of the elongate member with the access site 1000 during a surgical procedure. In some embodiments, the system 100 may further include a patient platform 104 configured to support the patient 999 during a surgical procedure. An elongate member (not shown) may be inserted into the patient 999 at an access site 1000, as shown in FIGS. 2A and 2B. The patient platform 104 may be supported by a floor support 102, which may generally sit upon a floor of an operating room. In some embodiments, the alignment joint 106 and/or the longitudinal support rail 108 may be draped with a sterile drape, as described in U.S. Pat. No. 8,602,031, which is herein incorporated by reference. In some embodiments, the alignment joint 106 and/or and the longitudinal support rail 108 may maintain the alignment of the elongate member with the access site 1000 through the sterile drape.

Figure 2C:
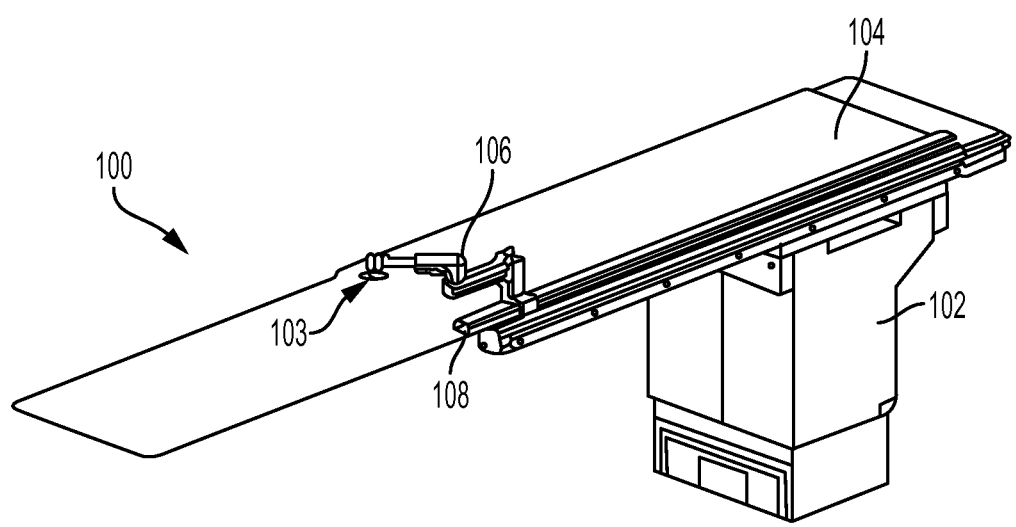

In some embodiments, as shown in FIGS. 2A-2D, the system 100 may further include a stabilizer 103 coupled to a distal portion of one support arm of the alignment joint 106. The stabilizer 103 may be configured to couple the distal portion of one support arm of the alignment joint 106 to the patient 999. In some embodiments, as shown in FIGS. 2A-2C, the alignment joint 106 may be configured to position a stabilizer 103 at the access site 1000 of the patient 999. In operation, the alignment joint 106 may align a second support structure with the access site. In some embodiments, a position of the access site 1000 may be communicated by the alignment joint 106 to the second support structure. For example, a second support structure may include a revolute joint carrying an instrument driver or a base of an active drive device. In some embodiments, a heading direction of the instrument driver or active drive device may be adjustable, to ensure alignment of the elongate member with the access site 1000. The alignment joint 106 may include position sensors, such that the alignment joint 106 may be used to align an instrument driver or a revolute joint carrying the instrument driver with the access site 1000 during a surgical procedure.

Figure 2D:
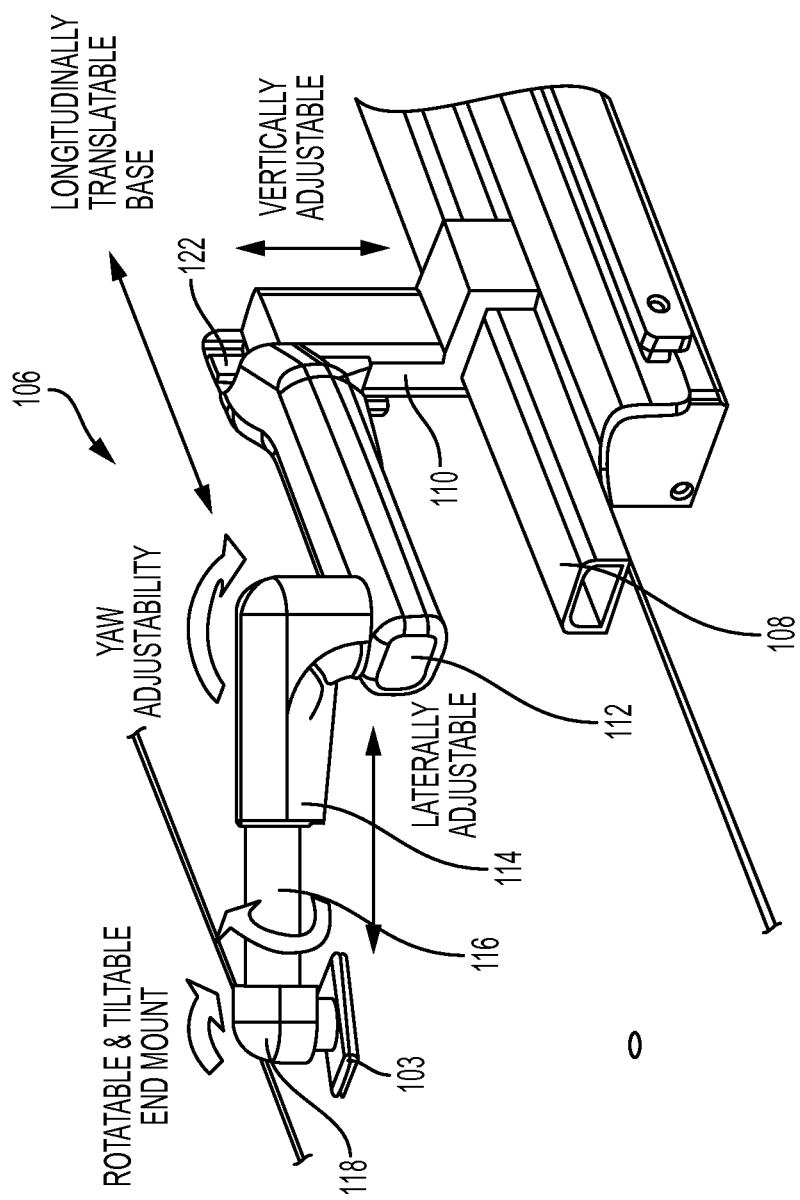

As shown in FIG. 2D, an alignment joint 106 may include a longitudinally oriented support rail 108, such that the support rail 108 is longitudinally oriented with respect to the patient platform 104 and general positioning of patient 999 thereon, as shown in FIGS. 2A and 2B. The support rail 108 may carry one or more support arms of the alignment joint 106. As shown in FIG. 2D, the one or more support arms may include a vertically extending arm 110, which is moveable along the longitudinal support rail 108. The vertically extending arm 110 may couple to an upper arm 112, which may be vertically adjustable with respect to the arm 110 and/or the patient platform 104. For example, the upper arm 112 may include a rail section 122 that is received in a corresponding slot (not shown), allowing vertical movement of the upper arm 112.

In some embodiments, as shown in FIG. 2D, the one or more support arms of the alignment joint 106 may include a lateral arm assembly, which is pivotally supported on the upper arm 112. The lateral arm assembly may generally support the stabilizer 103 and facilitate movement of the stabilizer 103 across the patient platform 104, for example in a direction perpendicular to the longitudinal support rail 108 and alignment of the stabilizer with the access site 1000. As shown in FIG. 2D, the one or more support arms of the alignment joint 106 may be adjustable in a yaw and/or pitch orientation. In some embodiments, as shown in FIG. 2D, the lateral arm assembly may include a pivoting arm support 114, which is pivotally secured to the upper arm 112. Accordingly, the pivoting arm support 114 may facilitate yaw adjustment of the alignment joint 106. Further, an extension arm 116 may be received within the pivoting arm support 114, and may be configured to translate with respect to the pivoting arm support 114 to allow selective extension and retraction with respect to the pivoting arm support 114. The stabilizer 103 may be maneuverable at a distal end of the extension arm 116 using a rotatable, tiltable, or pivotable joint 118.

Figure 3A:
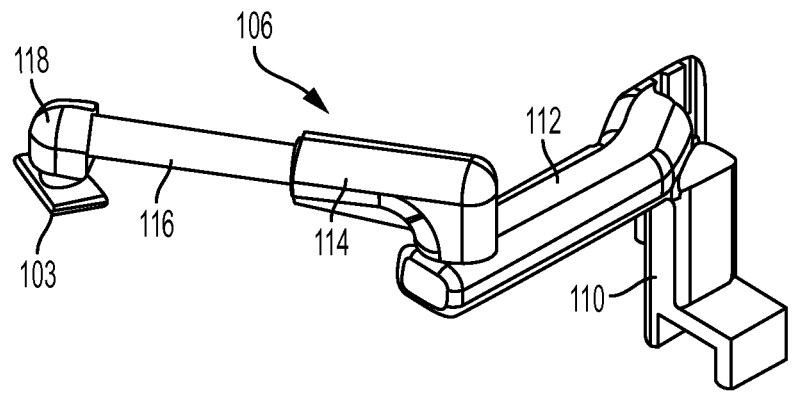
FIGS. 3A-E illustrate perspective views of an alignment joint, in accordance with one embodiment.
Figure 3B:
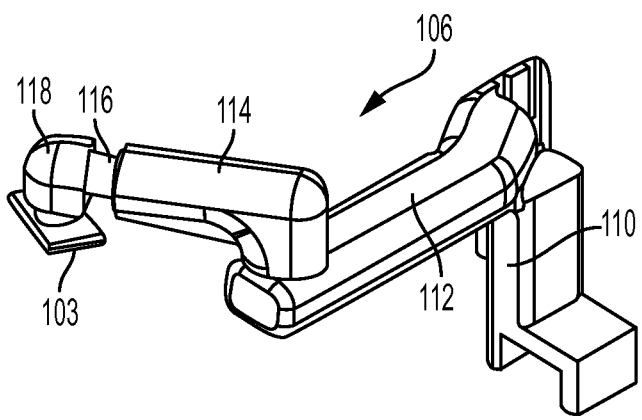
Figure 3C:
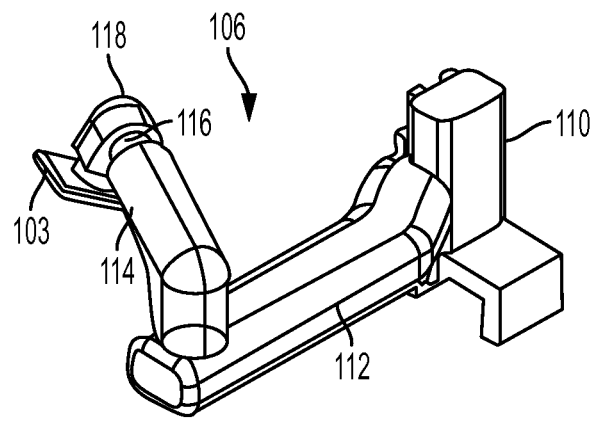
Figure 3D:
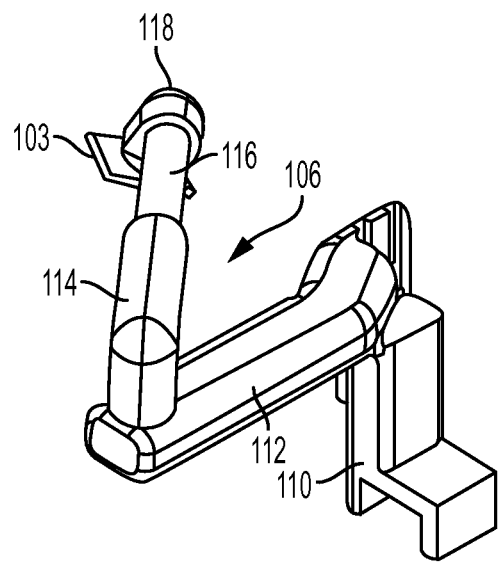
Figure 3E:
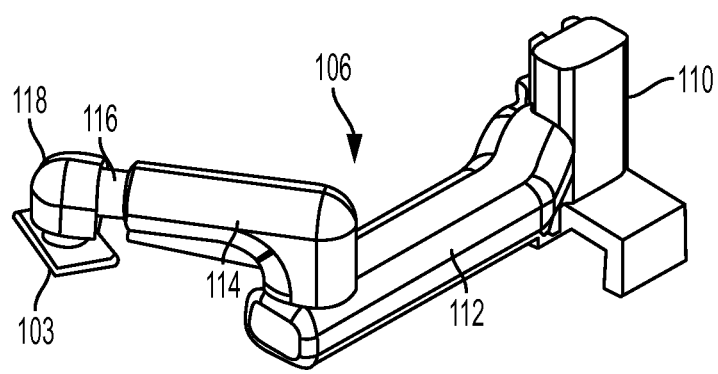

FIGS. 3A-3E illustrate various positions of the support arms of the alignment joint 106. As shown in FIG. 3A, the alignment joint 106 is illustrated initially with the extension arm 116 extended away from the pivoting arm 114. As shown in FIG. 3B, the extension arm 116 may move toward the pivoting arm 114. In some embodiments, the extension arm 116 may compress or accordion to be positioned in the pivoting arm 114. Alternatively, the length of the pivoting arm 114 may be substantially equal to the length of the extension arm 116, such that the pivoting arm 114 receives the extension arm 116 in a slot of the pivoting arm 114. As shown in FIG. 3C, the pivoting arm 114 may rotate about the upper arm 112, and the upper arm 112 may also be lowered relative to the vertically extending arm 110. In some embodiments, as shown in FIG. 3D, the extension arm 116 may be extended from the pivoting arm 114 upon rotation of the pivoting arm 114 about the upper arm 112. Further, the upper arm 112 may be in an uppermost position, the extension arm 116 may be in a partially extended position, and the joint 118 may be rotated away from the vertically extending arm 110. As shown in FIG. 3E, the pivoting arm 114 may be rotated about the upper arm 112 as compared with the position shown in FIG. 3C. The vertically extending arm 110, upper arm 112, pivoting arm 114, extension arm 116, and joint 118 may generally be placed in any relative position that is desired, facilitating placement of the stabilizer 103 at or adjacent an access site (not shown in FIGS. 3A-3E) of a patient. Each component of the alignment joint may be rotatable, tiltable, or pivotable by a ball and socket, knuckle, revolute, turnbuckle, or pin joint. Alternatively, one or more joints may be fixed.

Further, movement of each of the support arms of the alignment joint 106 may be remotely controllable, or otherwise capable of being manipulated or moved by a user. For example, the alignment joint 106 may include one or more position sensors for aligning a revolute joint carrying the instrument driver with the location and/or position of the access site 1000. Alternatively, the alignment joint 106 may include one or more position sensors for aligning an active drive device with the location and/or position of the access site 1000. In some embodiments, angle and/or position encoders may be provided at each joint of the alignment joint 106, for example, between (a) the rail 108 and arm 110, (b) the arm 110 and upper arm 112, (c) the upper arm 112 and pivoting arm support 114, (d) the pivoting arm support 114 and the extension arm 116, (e) the extension arm 116 and the joint 118, and/or (f) the joint 118 and the stabilizer 103. Further, position of the stabilizer 103 relative to the access site 1000, as well as the other components of the alignment joint 106, may be accurately determined.

In some embodiments, the various joints in the alignment joint 106 may be manually lockable, for example to lock the alignment joint 106 or portions thereof into a fixed position. In this manner, portions of the alignment joint 106 may be held fixed while other portions are capable of being moved, for example to effect movement of an elongate member. Additionally, the alignment joint 106 may comprise one or more quick release switches to unlock the joints.

In some embodiments, movement of the instrument drive or active drive device may be effected by the alignment joint 106 and any component(s) thereof, during a surgical procedure. For example, moving the vertically adjustable arm 110 up and down above the patient access site 1000 may robotically adjust the vertical position of the robotic catheter system, for example an instrument driver and/or elongate member. Additionally or alternatively, moving the laterally adjustable arm member 112, yaw adjustable arm member 114, and longitudinally translatable base along the longitudinal rail 108 about the patient access site 1000 may result in adjustment of the longitudinal and yaw position of the instrument driver, revolute joint, active drive device and/or components thereof.

In some embodiments, a system for aligning an elongate member with an access site may include a revolute joint, an alignment joint, and at least one position sensor. A revolute joint may be configured to support an instrument driver, such that the revolute joint is longitudinally translatable relative to an operating table and the instrument driver is configured to axially and laterally displace an elongate member. An alignment joint, as described above, may be longitudinally translatable relative to the operating table and configured to align the elongate member with the access site. In some embodiments, the at least one position sensor may provide feedback to the revolute joint, such that the revolute joint aligns the instrument driver with the access site and communicates the location of the access site with the instrument driver such that the instrument driver knows when to stop advancing and not hit the patient.

Figure 4:
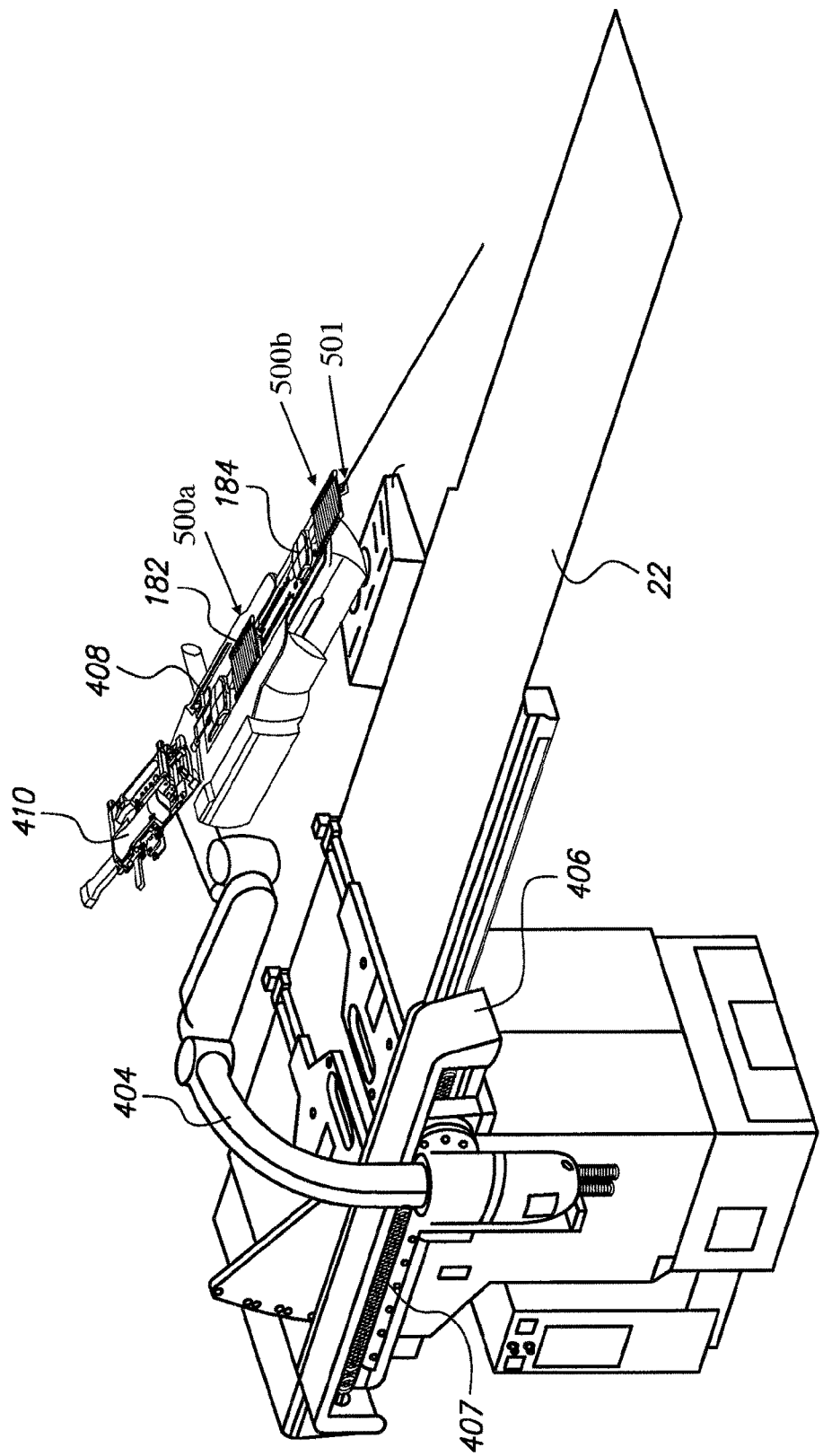
FIG. 4 illustrates an instrument driver and revolute joint, in accordance with one embodiment.

FIG. 4 illustrates an instrument driver 408 and a revolute joint 404 positioned on a rail 407, in accordance with a system for aligning an elongate member with an access site. The system preferably functions to axially and/or rotationally drive an elongate member into an access site of a patient.

In some embodiments, as shown in FIG. 4, the instrument driver 408 includes a catheter drivable assembly 182 for positioning a catheter, and a sheath drivable assembly 184 for positioning a sheath that is placed coaxially around the catheter. In the illustrated embodiments, the sheath drivable assembly 184 is moveable relative to the catheter drivable assembly 182. The instrument driver assembly 408 may further include a guide wire manipulator 410 for positioning a guidewire (not shown) that may be placed within a lumen of the catheter. In some embodiments, a stabilizer at an access site of the patient may be in communication with the instrument driver, such that the elongate member driven by the instrument driver is aligned with the access site and will not drive past the access site and injure the patient.

In some embodiments, the instrument driver 408 may further include two anti-buckling devices 500a, 500b for preventing the buckling of the catheter and the sheath during use. A coupler 501 at the distal end of the anti-buckling device 500b may couple, attach, or fasten to a stabilizer at the access site of the patient, as described above, such that the elongate member supported by the anti-buckling device is aligned with the access site.

In some embodiments, as shown in FIG. 4, the instrument drive 408 may be supported by a revolute joint 404. In some embodiments, the revolute joint 404 may be mounted to the patient support (table) 22 via a rail system 406. The rail system 406 may allow the revolute joint 404 (and therefore, the instrument driver 408) to translate along the length of the patient support 22. In some embodiments, the rail system 406 includes a motorized rail 407, which can be actuated to drive movement of the revolute joint 404. In other embodiments, other mechanisms may be used, including but not limited to a lead screw, a ball screw, linear motor, belt, and/or cable drive, etc. In other embodiments, the revolute joint 404 may be allowed to move by actuating a button at the revolute joint 404, thereby releasing the revolute joint 404 from a locked position against the rail system 406. The revolute joint 404 can then be translated manually along the axis of the patient support 22. When the revolute joint 404 has reached a desired position, the button may be released to lock the revolute joint 404 at the desired position. The revolute joint has been described in U.S. Pat. No. 7,789,874, filed on Jul. 1, 2005, the entire disclosure of which is expressly incorporated by reference herein.

Figure 5:
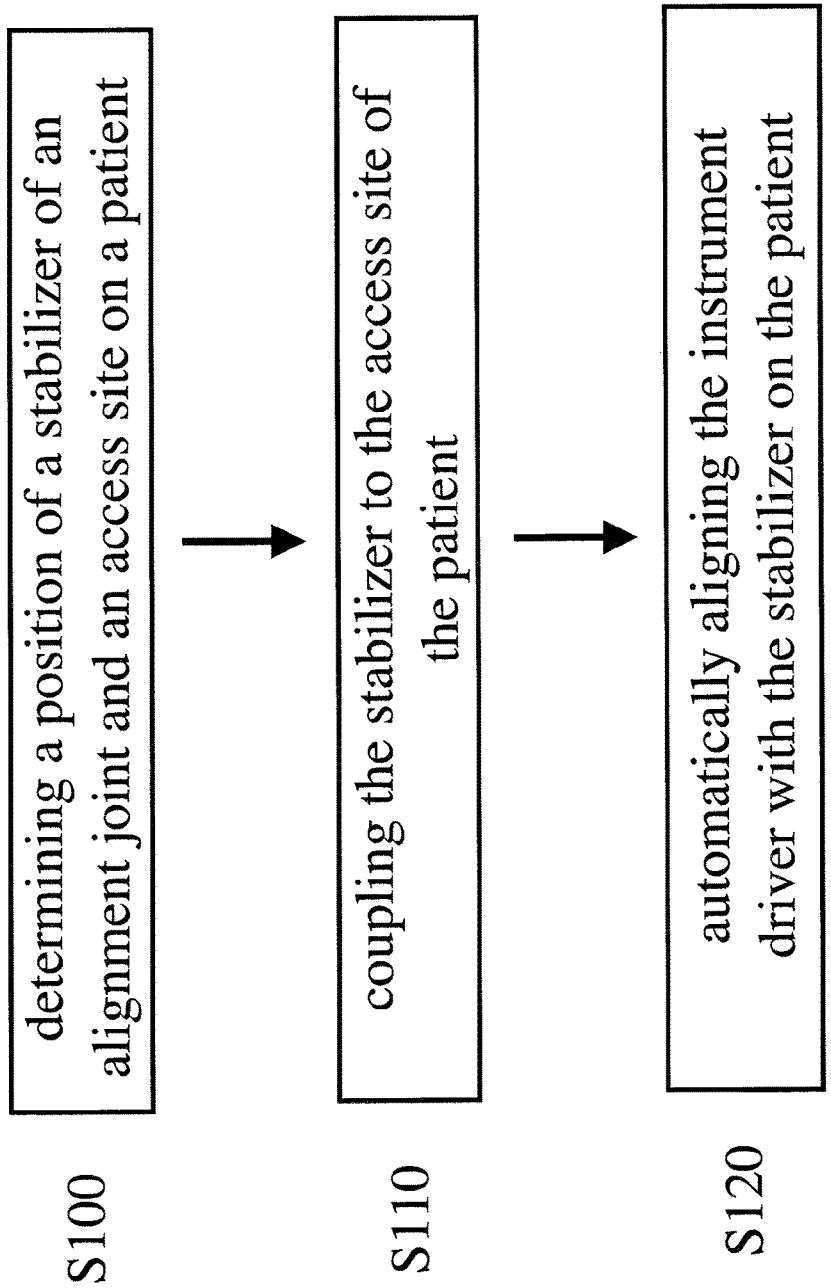
FIG. 5 is a flow chart of a method of aligning an elongate member with an access site, in accordance with one embodiment.

FIG. 5 illustrates one embodiment of a method for aligning an elongate member, controlled by an instrument driver, with an access site. According to this embodiment, the method includes determining a position of a stabilizer of an alignment joint and the access site on a patient S100; coupling the stabilizer to the access site on the patient S110; and automatically aligning the instrument driver with the stabilizer on the patient S120. The method preferably functions to maintain alignment of an elongate member with an access site of a patient during a surgical procedure.

As shown in FIG. 5, the method may involve determining a position of a stabilizer of an alignment joint and the access site on a patient S100. In some embodiments, an alignment joint may include one or more position sensors, such that a position of a stabilizer and thus an access site may be determined. The position of the access site may be communicated to a revolute joint supporting an instrument driver or to a base of an active drive device, such that the elongate member driven by the instrument driver or active drive device may be aligned with the access site and not overrun the access site.

As shown in FIG. 5, the method may further involve coupling the stabilizer to the access site on the patient S110. Once a position of the access site is determined by one or more position sensors on the alignment joint, the stabilizer coupled to the alignment joint may be adhered, coupled, or otherwise fastened to the patient near the access site, such that the position of the stabilizer marks the access site.

As shown in FIG. 5, the method may also involve automatically aligning the instrument driver with the stabilizer on the patient S120. As described above in step S110, the stabilizer marks a position of the access site. In some embodiments, the position of the access site may be communicated to a revolute joint and/or instrument driver. The instrument driver may then be aligned with the stabilizer on the patient, such that the elongate member driven by the instrument driver may be aligned with the access site.

In some embodiments, the method of FIG. 5 may further include the step of coupling an anti-buckling mechanism of an instrument driver or an active drive device to the stabilizer of the alignment joint. As described above in connection with FIG. 4, an anti-buckling mechanism for supporting the elongate member may be coupled to the stabilizer at the access site, such that the elongate member may be driven into the access site. Alternatively, an active drive device may be coupled to the stabilizer. In some embodiments, the active drive device may axially translate the elongate member towards an access site of a patient. Exemplary active drive devices are described in pending U.S. patent application Ser. Nos. 13/803,535; 13/803,627; 13/801,957; 13/832,352; 13/833,531; 13/835,136; 13/839,967; and 13/838,777, each of which are herein incorporated by reference.

In some embodiments, the method of FIG. 5 may further include automatically adjusting an alignment of the stabilizer with the access site if the access site changes position (for example, if the patient moves on the table). In some embodiments, the method may further include automatically adjusting an alignment of the instrument driver with the stabilizer if the stabilizer changes position.

It will be appreciated that the mechanisms and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, this disclosure may be practiced otherwise than is specifically explained and illustrated, without departing from its spirit or scope. Various alternatives to the embodiments described herein may be employed in practicing the claims, without departing from the spirit and scope as defined in the following claims. The scope of the disclosure should be determined, not with reference to the above description, but instead with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. An alignment system for controlling an alignment of a robotically controlled elongate member at an access site on a patient, the system comprising:
   a longitudinal support rail;
   multiple support arms coupled with and extending from the longitudinal support rail to form an alignment joint, wherein the support arms are configured to reach the access site on the patient, and wherein the support arms are configured to maintain the alignment of the elongate member with the access site during a surgical procedure;
   a stabilizer comprising:
      a base with an opening formed therethrough for receiving the elongate member, and
      a connector that couples an active drive device to the stabilizer, the connector comprising an outwardly exposed extension with a slot formed thereunder, the connector configured to directly attach the active drive device to the stabilizer via the slot; and
   a port configured to be inserted at the access site, wherein the stabilizer is aligned with the port,
   wherein one of the support arms is configured to be attached to the stabilizer to support and facilitate rotational movement of the stabilizer with respect to the support arm when the stabilizer is attached to the support arm.

2. The alignment system of claim 1, wherein the longitudinal support rail is attached to a patient support.

3. The alignment system of claim 2, wherein the support arms and the longitudinal support rail are draped with a sterile drape.

4. The alignment system of claim 3, wherein the support arms and the longitudinal support rail maintain the alignment of the elongate member through the sterile drape.

5. The alignment system of claim 1, wherein the support arms form at least one rotatable joint configured to adjust a yaw orientation of the elongate member.

6. The alignment system of claim 1, wherein at least one of the support arms is adjustable in a yaw orientation.

7. The alignment system of claim 1, wherein at least one of the support arms is adjustable in a pitch orientation.

8. The alignment system of claim 1, wherein the stabilizer is coupled to a distal portion of one of the support arms.

9. The alignment system of claim 1, wherein the stabilizer is coupled to a distal portion of one of the support arms, and further comprising an anti-buckling device coupled to the stabilizer and supporting the elongate member.

10. The alignment system of claim 1, wherein the active drive device is coupled to a distal portion of one of the support arms, and wherein the active drive devices inserts and retracts the elongate member.

11. The alignment system of claim 1, further comprising at least one sensor configured to determine a position of the access site.

12. The alignment system of claim 11, further comprising an instrument driver on a second support structure, wherein a position of the access site is communicated to the second support structure, and a heading direction of the instrument driver is adjustable to ensure alignment of the elongate member with the access site.

13. A system for aligning an elongate member with an access site on a patient, the system comprising:
a revolute joint configured to support an instrument driver, wherein the revolute joint is translatable relative to an operating table, and wherein the instrument driver is configured to axially and laterally displace an elongate member;
an alignment joint coupled to the revolute joint, wherein the alignment joint is translatable relative to the operating table, and wherein the alignment joint is configured to align the elongate member with the access site, the alignment joint comprising one or more position sensors, wherein an output of the one or more position sensors is indicative of a position of the alignment joint; and
a stabilizer engageable with the patient, wherein the stabilizer comprises a base with an opening formed therethrough for receiving the elongate member, wherein the output of the one or more position sensors is further indicative of a position of the stabilizer;
wherein the system is configured to: determine the position of the stabilizer based on the output of the one or more position sensors and automatically move the revolute joint to align the instrument driver with the stabilizer based on the determined position of the stabilizer.

14. The system of claim 13, wherein the stabilizer is configured to couple to an anti-buckling mechanism of the elongate member.

15. The system of claim 13, further comprising an active drive device attached to the stabilizer, wherein the active drive device inserts and retracts the elongate member.

16. The system of claim 13, wherein the stabilizer is coupled to the alignment joint.

17. A system for aligning an elongate member with an access site on a patient, the system comprising:
an alignment joint, wherein the alignment joint is translatable relative to a patient support, and wherein the alignment joint is configured to align an elongate member with the access site;
an active drive device coupled to the alignment joint, wherein the active drive device is configured to manipulate the elongate member at the access site; and
a stabilizer connected to the active drive device by a connector, wherein the stabilizer comprises a base with an opening formed therethrough for receiving the elongate member, and wherein the connector comprises an outwardly exposed extension with a slot formed thereunder, the connector configured to directly attach the active drive device to the stabilizer via the slot,
wherein the alignment joint is configured to be attached to the stabilizer to support and facilitate rotational movement of the stabilizer with respect to the support arm when the stabilizer is attached to the support arm.

18. The system of claim 17, wherein the active drive device axially translates the elongate member.

19. A method of aligning an elongate member, controlled by an instrument driver, with an access site, the method comprising:
coupling a stabilizer to the access site on a patient, wherein the stabilizer is engageable with the patient, wherein the stabilizer comprises a base with an opening formed therethrough for receiving the elongate member;
coupling the stabilizer to an alignment joint, the alignment joint comprising at least one position sensor;
determining a position of the alignment joint based on an output of the at least one position sensor;
determining a position of the stabilizer based on the output of the at least one position sensor; and
automatically aligning the instrument driver with the stabilizer on the patient based on the determined positions of the stabilizer and the alignment joint.

20. The method of claim 19, further comprising coupling at least one of an anti-buckling mechanism of an instrument driver or an active drive device to the stabilizer of the alignment joint.

* * * * *